(12) United States Patent
Hwu

(10) Patent No.: US 7,129,484 B2
(45) Date of Patent: Oct. 31, 2006

(54) METHOD FOR PATTERN RECOGNITION IN ENERGIZED CHARGE PARTICLE BEAM WAFER/SLIDER INSPECTION/MEASUREMENT SYSTEMS IN PRESENCE OF ELECTRICAL CHARGE

(75) Inventor: Justin Hwu, San Jose, CA (US)

(73) Assignee: Hitachi Global Storage Technologies Netherlands B.V., Amsterdam (NL)

( * ) Notice: Subject to any disclaimer, the term of this patent is extended or adjusted under 35 U.S.C. 154(b) by 469 days.

(21) Appl. No.: 10/761,749

(22) Filed: Jan. 21, 2004

(65) Prior Publication Data

US 2005/0157918 A1   Jul. 21, 2005

(51) Int. Cl.
*G06F 19/00* (2006.01)
*G01N 23/00* (2006.01)

(52) U.S. Cl. .................. 250/307; 250/492.1; 700/121
(58) Field of Classification Search ............... 250/307, 250/492.22; 700/121
See application file for complete search history.

(56) References Cited

U.S. PATENT DOCUMENTS

| 5,302,828 | A | 4/1994 | Monaham .................. 250/307 |
| 5,916,424 | A | 6/1999 | Libby et al. ............ 204/298.36 |
| 6,332,962 | B1 | 12/2001 | Athas et al. ........... 204/192.34 |
| 6,476,398 | B1 | 11/2002 | Xu et al. ..................... 250/396 |
| 6,521,890 | B1 | 2/2003 | Ishitani et al. .............. 250/309 |
| 6,587,581 | B1 | 7/2003 | Matsuyama et al. ........ 382/149 |
| 2002/0158199 | A1 | 10/2002 | Takane et al. .............. 250/310 |
| 2002/0185597 | A1 | 12/2002 | Ikku et al. .................. 250/309 |

FOREIGN PATENT DOCUMENTS

| JP | 2226001 | 9/1990 |
| JP | 7254387 | 10/1995 |
| JP | 7312195 | 11/1995 |

OTHER PUBLICATIONS

Kurt Laken; "Advanced Pole Analysis: A New Tool for Measuring Pole Tip Recession". VEECO Brochure (2002).

*Primary Examiner*—Evan Pert
(74) *Attorney, Agent, or Firm*—John L. Rogitz

(57) ABSTRACT

To account for changing image contrast due to wafer/slider/mask charging in e-beam or ion beam wafer/slider/mask inspection or measurement tools, which could lead to false pattern recognition comparison and result in coordination verification failures, if a site of a wafer/slider/mask being inspected fails a pattern recognition test when compared to a first template, a second template configured with a different contrast is used for a second pattern recognition comparison after the tools starts stage search. Use of image histogram analysis principles can also be applied for interpolation or extrapolation of the two image templates for generating of a third template with a different image contrast from the first two for customizing template contrast for further pattern recognition robustness fine tuning. This synthesized template can serve as the "second" template or even be used as the third template in certain conditions where change of charging behavior from different production batches is seen over a time period.

13 Claims, 2 Drawing Sheets

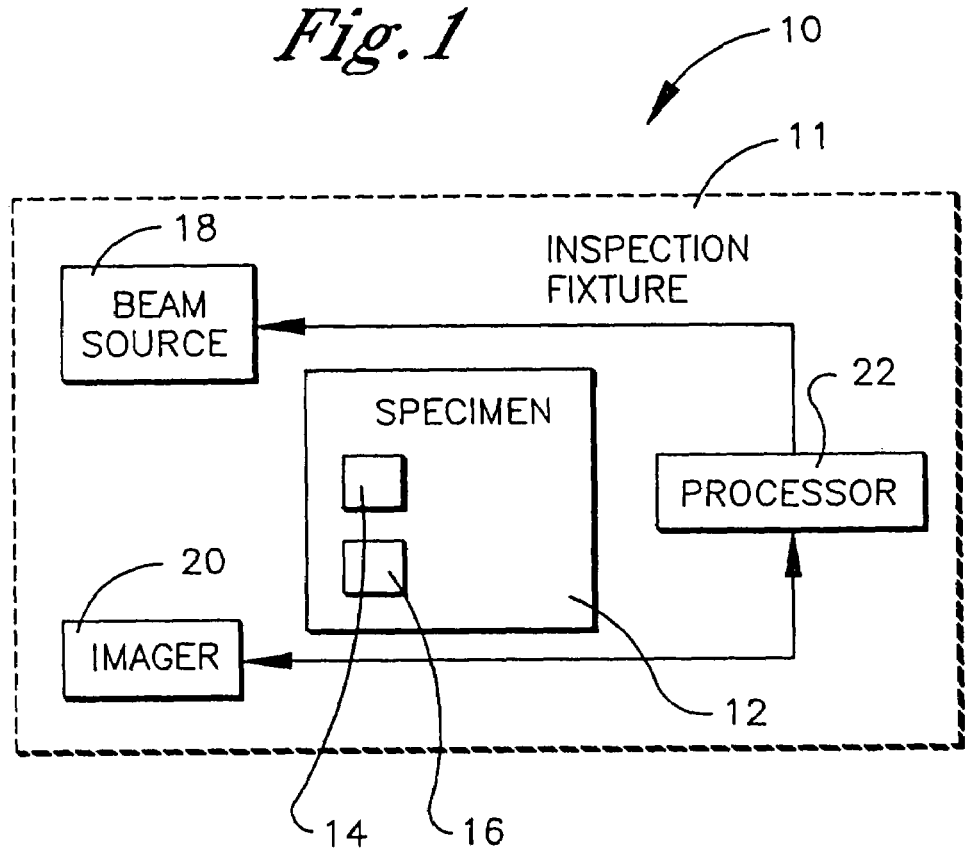
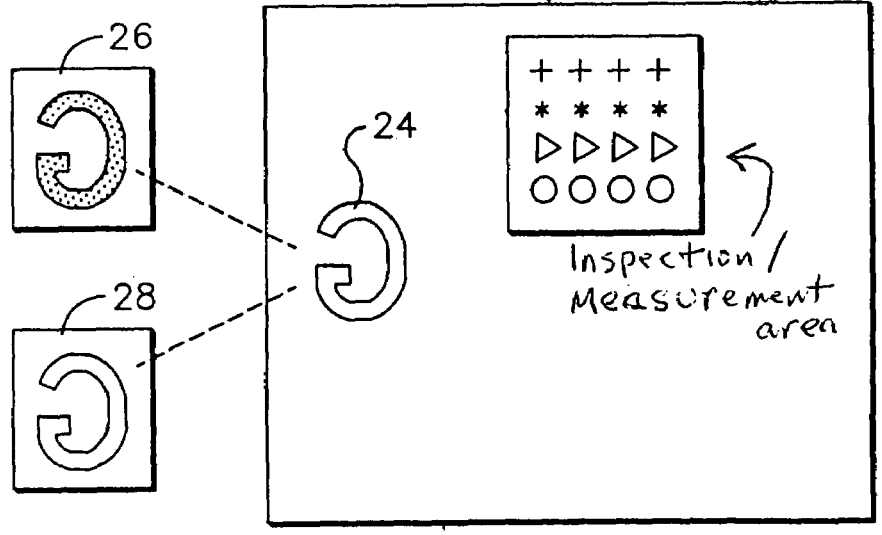

METHOD FOR PATTERN RECOGNITION IN ENERGIZED CHARGE PARTICLE BEAM WAFER/SLIDER INSPECTION/MEASUREMENT SYSTEMS IN PRESENCE OF ELECTRICAL CHARGE

FIELD OF THE INVENTION

The present invention relates generally to pattern recognition of semiconductor and data storage wafers and masks using ion beam and electron beam (e-beam) inspection.

BACKGROUND

Wafers and masks, including those non-silicon wafers and photomasks used in, e.g., hard disk drive read/write heads and optical device fabrication, typically are inspected for defects and/or measured for device critical dimension control using electron beam (e-beam) or ion beam systems utilizing beam scanning for image-based defect analysis or measurements. The systems used include scanning electron microscopes (SEM) for failure analysis and defect review, focused ion beam (FIB) systems, and critical dimension scanning electron microscopes (CDSEM). During the inspection or measurement process of a feature of interest on a specimen placed on a mechanical stage, the system acquires an image of a portion of the targeted area on the specimen after the stage is moved to the predetermined coordinates, and the system software compares the image to a pre-stored image template for location registration verification so that the correct feature of interest can be identified prior to the final inspection or measurement execution. The acquired image after stage move is compared with the stored image template and the unique pattern recognition feature in the image is identified using pattern recognition principles. If the comparison fails, the system understands that the first stage move is not successfully bringing the electron/ion imaging optics close to the targeted area. The test might subsequently start executing a so-called stage search movement, usually a spiral search method with gradual radial distance increase accompanied by stage move around the first stage move coordinates, to determine whether any subsequent image acquired after each stage search contains the unique pattern in the image templates. Stage search and the accompanying image acquisition can be time-consuming, adversely affecting specimen inspection or measurement throughput and thus the production cycle time.

As understood herein, complicating the above process is the fact that during the imaging acquisition process it is possible for certain types of specimen, e.g., photoresist with the combination of either top or bottom antireflective coating layers (TARC or BARC) or photoresist on insulator under layer on a wafer, or chrome patterned layer on glass substrate for a photomask, to become charged as the result of being repeatedly exposed to the imaging beam, e.g., during the accompanying image acquisition after each stage move in the stage search procedure. Charging of the specimen is frequently encountered when inspection/failure analysis SEM, CDSEM and FIB inspection fixtures are used. The charge on the specimen changes the contrast of the image vis-á-vis the first image obtained from a fresh uncharged specimen. This charge-induced contrast change in turn results in false coordination verification failures, precipitating unnecessary stage searches and results in pattern recognition failures during automatic specimen inspection and measurement. Various pattern recognition algorithms have been developed that attempt to filter out contrast changes caused by charging but these algorithms do not work well, they generally are case-specific, and they typically require considerable user experience to function.

SUMMARY OF THE INVENTION

A method to account for image contrast variation due to specimen charging in e-beam or ion beam wafer inspection and measurement tools includes, if a site on a specimen being imaged fails a pattern recognition test when compared to a first template, using a second template configured with a different contrast than the first template for a second comparison with the site.

In the preferred embodiment the second template is used in the event of a failure after executing a stage search in response to the failure.

As set forth further below, the first template may be derived from a first image frame of a first portion of the wafer when the location is initially imaged by an e-beam or by an ion beam. On the other hand, the second template may be derived from a second image frame of the same (first) portion of the specimen obtained after substantial electrical charge has been induced in the specimen. The method may also include, if desired, interpolating between the first and second templates to derive an intermediate template having a contrast different from those of the first two templates.

In another aspect, a wafer/slider or mask inspection/measurement system includes a source of an imaging beam. The energized charge source may be an electron beam or ion beam. A processor receives images of portions of specimen irradiated by the imaging beam to execute logic that includes obtaining a first template from a first image frame of a first location on the specimen when the first location is substantially free of electric charge, and obtaining a second template from a second image frame of the first location on the specimen when the first location is substantially electrically charged. The logic also includes using the templates to execute an inspection/measurement sequence of multiple sites on the specimen.

In still another aspect, a computerized specimen inspection/measurement system includes first means for comparing, using pattern recognition, an image of a portion of specimen to a first template. The system also includes means for determining whether the portion passes or fails based on the first comparing means. Also, the system includes second means for comparing, in response to the means for determining and using pattern recognition, an image of the portion of specimen to a second template, with the means for determining whether the portion passes or fails based on the second comparing means.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a block diagram of an exemplary specimen inspection/measurement fixture that can use, e.g., SEM or FIB principles;

FIG. 2 is a schematic diagram of an area of a specimen as generated by an SEM or FIB imager, showing two templates derived therefrom.

DETAILED DESCRIPTION OF THE PREFERRED EMBODIMENT

Figure 3:
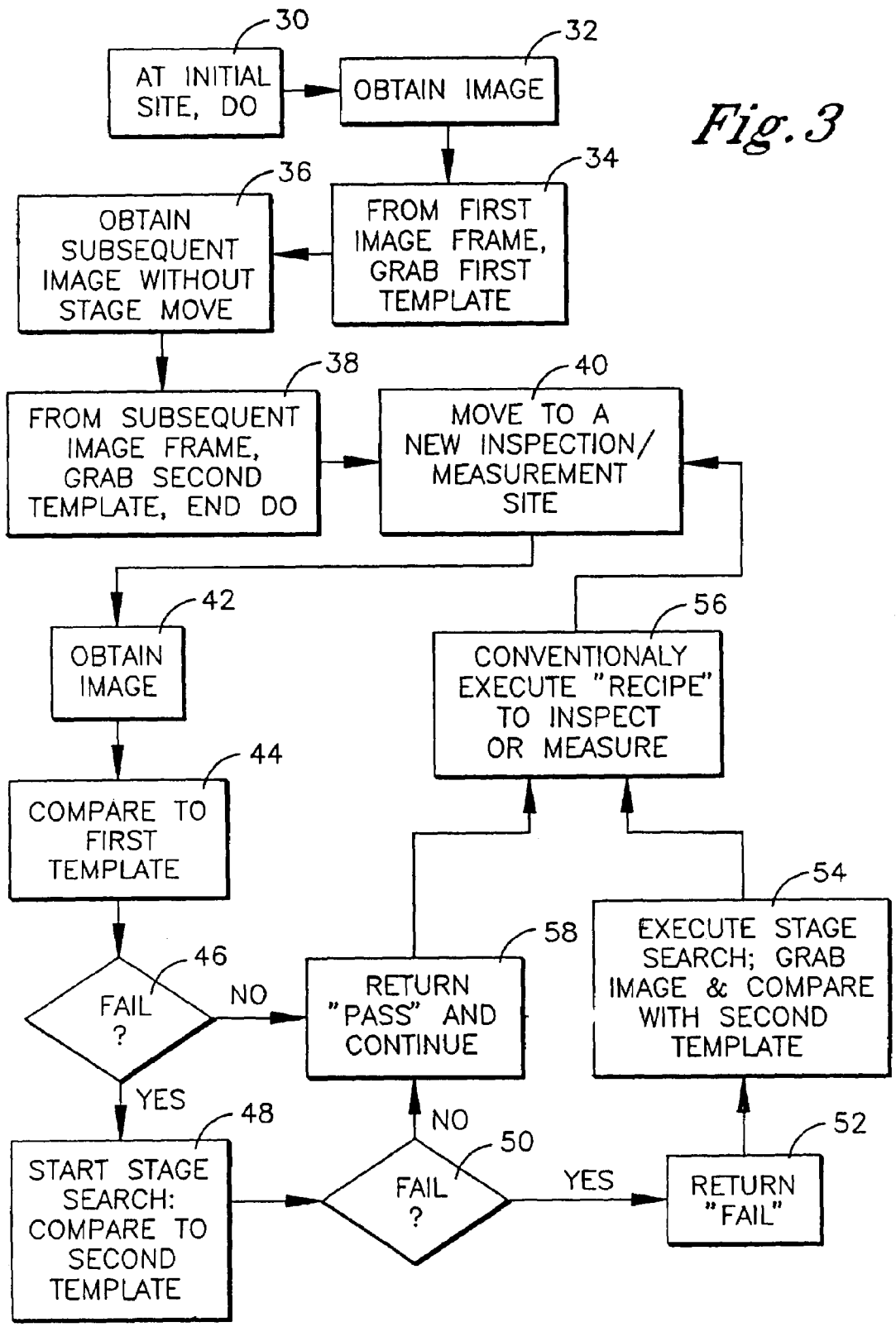
FIG. 3 is a flow chart of the present logic.

Referring initially to FIG. 1, a system is shown, generally designated 10, which includes an inspection or measurement fixture 11 through which a specimen 12 such as might be used for making, e.g., semiconductor devices, hard disk drives, and other optical devices, can be conveyed to inspection or measurement of critical dimensions. Each specimen 12 may have plural target arrays 14, 16 that are identical to each other. The patterns that must be inspected or measured in the target arrays 14, 16 may include line/space, pitch, contact holes, designed patterns, and so on.

As used herein, a "specimen" can be a wafer, a mask (also referred to as a photomask), or a slider on a stage, or any combination thereof. For example, a specimen can be a photomask that can include a very thin layer of metal chromium on an insular substrate made of glass or quartz. The chrome layer, which can be etched into patterns for subsequent pattern transfer to wafers using photolithography, is susceptible to charging as recognized herein, and hence is amenable to the advantgaes provided by the present method.

A beam source 18 such as an ion beam source or electron beam source irradiates the specimen 12 with ion or electron beams as they pass through the fixture 11 to scan the specimen 12 in accordance with principles known in the art such that an imager 20 (including a detector or a detector combination) received signals from the scanned areas and forms images of them. The imager 20 and beam source 18 can be controlled by a processor 22 that executes the logic below as might be embodied in hardware- and/or software-implemented logic circuits. With the exception of the logic disclosed herein, the fixture 11 may be a conventional wafer, slider, or mask inspection system, preferably under vacuum. The imager 20 may include the processor 22 and/or beam scan control circuitry and detectors for imaging signal collection and processing.

FIG. 2 shows a portion 14 or 16 in the specimen 12 with a unique code symbol 24 such as a backward "G". It is to be understood that the code symbol 24 may be any unique feature or pattern in all portions on the specimen. The unique code symbol 24 may be scanned at least twice to generate at least first and second templates 26, 28, once initially when the specimen 12 bears no electric charge and again after scanning from the beam source 18 has induced an electrical charge on the specimen 12. As shown in FIG. 2, the templates 26, 28 are identical to each other, except that the image on the first template 26 has a contrast that is different from the contrast of the image on the second template 28.

Attention is now turned to FIG. 3, which indicates at block 30 that at an initial site or portion the logic of blocks 32–38 is performed for building the pattern recognition templates in an inspection/measurement recipe. Moving to block 32, an initial image is obtained of the site, and at block 34 the first template is obtained by grabbing the image frame. Since this is the first image, the specimen has not yet been irradiated sufficiently to become totally charged, and the first template consequently has a contrast that corresponds to the minimal or indeed absence of electrical charge.

Next, at block 36 a subsequent image of the same portion of the specimen is obtained without any stage move and the same unique symbol or feature 24 is grabbed again from this second image to establish a second template at block 38. At this point the initial area on the specimen has been imaged twice, so that the contrast of the image on the second template, depending as it does on the induced charge, is different from the contrast of the image on the first template. Both templates are saved and the DO loop ends.

At block 40, the logic moves the specimen to a new site for inspection with the help of pattern recognition principles, i.e., the actual specimen inspection or measurement commences after the successful pattern recognition. To do this, an image of the subsequent portion is obtained at block 42 after the first stage move to the first inspection or measurement location and the image is compared to the first template. If pattern recognition techniques indicate a failure at decision diamond 46, the specimen is moved by stage search and a second image of the portion is acquired and compared to the second template at block 48. In this way, false failures arising from image contrast variations due to comparing a second charging image to the first template are reduced or even eliminated due to the fact that the stage search performs very small move so that the unique feature in the first image will still be somewhere in the second image and thus the same area including the feature is now exposed to the electron or ion beam twice. As a result of comparing the second image with the second template, the stage search will be robust and will need only a single step should the first pattern recognition using the first template fail after the specimen is moved to a new site. It is to be understood that in making the comparisons at decision diamonds 46 and 50, conventional pattern recognition principles may be used.

If the second comparison fails, the logic flows to block 52 to return "fail", and then to block 54 to execute a stage search such as a spiral search. On the other hand, if the first comparison at decision diamond 46 passed, the logic moves to block 58 to return "pass". In either case, the rest of the inspection or measurement "recipe" is conventionally executed at block 56, and then the logic loops back to block 40 to inspect or measure another site of the specimen 12. The upper limit of stage search step may be set to, e.g., five trials before an engineering level assist for template histogram interpolation or extrapolation is performed for tailoring templates for robust pattern recognition.

Additionally, while the use of two templates is disclosed, more templates may be generated if desired. For example, histogram information from the two templates can be used to predict how a new site or portion of the specimen will reveal contrast changes when undergoing multiple irradiation, using, e.g., interpolation. The difference in contrast between the two templates as found by histogram interpolation and subsequent imaging synthesis can be used to increase tolerance to process variation, e.g., to successfully perform pattern recognition steps on specimens produced weeks later that might result in slightly different charging behaviors, with the images consequently having contrasts somewhere between those of the first and second templates. As an example, suppose the first template above was grabbed from the initial image and then the second template was grabbed from the $N^{th}$ image. For a new specimen produced weeks later, the $N^{th}$ image might have a slightly different contrast than the second template, with interpolation or extrapolation (for even more greatly charged specimen) as appropriate using histogram analysis of the first and second templates being used to generate a modified second template for the comparison at step 50 in FIG. 3.

While the particular METHOD FOR PATTERN RECOGNITION IN ENERGIZED CHARGE PARTICLE BEAM WAFER/SLIDER INSPECTION/MEASUREMENT SYSTEMS IN PRESENCE OF ELECTRICAL CHARGE as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". It is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act". Absent express definitions herein, claim terms are to be given all ordinary and accustomed meanings that are not irreconcilable with the present specification and file history.

What is claimed is:

1. A method to account for changing image contrast due to specimen charging in e-beam or ion beam wafer/slider/mask inspection and measurement tools, comprising:
    if a site on a specimen being imaged fails a pattern recognition test when compared to a first template, using a second template configured with a different contrast than the first template for a second image comparison with the site.

2. The method of claim 1, wherein the second template is used in the event of a failure after executing a stage search in response to the failure.

3. The method of claim 2, wherein a stage search is executed only in the event of a failure using the first template.

4. The method of claim 1, wherein the first template is derived from a first image frame of a first site of the specimen, and the second template is derived from a second image frame of the first site of the specimen obtained after an electrical charge has been induced in the specimen.

5. The method of claim 1, further comprising:
    interpolating an image contrast between the first and second templates to derive an intermediate template.

6. An inspection/measurement system for wafers, sliders, and photomasks, comprising:
    a source of an imaging beam, the source being selected from the group consisting of: electron beam sources, and ion beam sources; and
    a processor receiving images of sites of a specimen irradiated by the imaging beam, the processor executing logic comprising:
    obtaining a first template from a first image frame of a first location on the specimen when the first location is relatively free of electric charge;
    obtaining a second template from a second image frame of the first location on the specimen when the first location is substantially electrically charged; and
    using the templates to execute an inspection of the specimen.

7. The system of claim 6, wherein the inspection uses pattern recognition tests for site coordination verification.

8. The system of claim 6, wherein the logic uses the second template in the event of a failure of a test using the first template after executing a stage search in response to the failure.

9. The system of claim 8, wherein the logic executes a stage search only in the event of a failure using the first template.

10. The system of claim 6, wherein the logic further comprises:
    interpolating image contrasts between the first and second templates to derive an intermediate template.

11. A computerized wafer test system comprising:
    first means for comparing, using pattern recognition, an image of a site of specimen to a first template;
    means for determining whether the site passes or fails based on the first comparing means; and
    second means for comparing, in response to the means for determining and using pattern recognition, an image of the site of the specimen to a second template, the means for determining whether the site passes or fails based on the second comparing means.

12. The system of claim 11, wherein the means for comparing and means for determining are implemented in hardware and/or software logic circuits.

13. The system of claim 11, comprising means for image contrast interpolation between the first and second templates to derive an intermediate template.

* * * * *